(12) United States Patent
Haymond

(10) Patent No.: US 9,155,811 B1
(45) Date of Patent: Oct. 13, 2015

(54) PACKAGED VENT STICK AIR FRESHENER WITH CUSTOM HEAD

(71) Applicant: American Covers, Inc., Draper, UT (US)

(72) Inventor: Bryce Haymond, Pleasant Grove, UT (US)

(73) Assignee: American Covers, Inc., Draper, UT (US)

( * ) Notice: Subject to any disclaimer, the term of this patent is extended or adjusted under 35 U.S.C. 154(b) by 483 days.

(21) Appl. No.: 13/688,970

(22) Filed: Nov. 29, 2012

Related U.S. Application Data

(60) Provisional application No. 61/566,161, filed on Dec. 2, 2011.

(51) Int. Cl.
*A61L 9/12* (2006.01)

(52) U.S. Cl.
CPC ........................ *A61L 9/12* (2013.01)

(58) Field of Classification Search
CPC .............. A61L 9/04; A61L 9/12; B05B 15/06
USPC ................................. 239/53, 55, 56
See application file for complete search history.

(56) References Cited

U.S. PATENT DOCUMENTS

| D176,671 | S | 4/1876 | Myers |
| 369,878 | A | 9/1887 | Palmer |
| 1,171,737 | A | 2/1916 | Madgan |
| 2,244,944 | A | 6/1941 | Furlonge |
| D140,109 | S | 1/1945 | Pierce |
| 2,642,248 | A | 6/1953 | Semon |
| 2,733,333 | A | 1/1956 | Peters |
| D177,826 | S | 5/1956 | Katz |
| D178,237 | S | 7/1956 | Katz |
| 3,239,145 | A | 3/1966 | Aurelio |
| 3,456,106 | A | 7/1969 | Mischa |
| 3,552,632 | A | 1/1971 | Wilson |
| 3,655,129 | A | 4/1972 | Seiner |
| 3,847,305 | A | 11/1974 | Tobin |
| 3,948,445 | A | 4/1976 | Andeweg |

(Continued)

FOREIGN PATENT DOCUMENTS

| CA | 2077251 | 5/1993 |
| EP | 0 348 970 | 1/1990 |

(Continued)

OTHER PUBLICATIONS

U.S. Appl. No. 29/435,389, filed Oct. 23, 2012; Aaron Irvin; notice of allowance dated Mar. 1, 2013.

(Continued)

*Primary Examiner* — Christopher Kim
(74) *Attorney, Agent, or Firm* — Thorpe North & Western, LLP

(57) ABSTRACT

An air freshener has a container with an open end. A sub-head has at least a portion releasably coupled across the open end of the container and closing the container with the front of the sub-head exposed. A vent rod extends from the back of the sub-head and into the container. A scent material has a desired scent carried by the vent rod and extending into the container with the vent rod. A supra-head has a back coupled to the front of the sub-head and a front with a face. The supra-head has a lateral dimension larger than a lateral dimension of the sub-head and covers the sub-head.

21 Claims, 8 Drawing Sheets

(56) References Cited

U.S. PATENT DOCUMENTS

| | | |
|---|---|---|
| 3,971,858 A | 7/1976 | Collier et al. |
| D246,986 S | 1/1978 | Costello |
| 4,084,079 A | 4/1978 | Costello |
| D250,041 S | 10/1978 | Schimanski |
| 4,149,675 A | 4/1979 | Van Breen et al. |
| 4,184,099 A | 1/1980 | Lindauer et al. |
| 4,214,146 A | 7/1980 | Schimanski |
| 4,226,944 A | 10/1980 | Stone et al. |
| D258,511 S | 3/1981 | Ashton |
| 4,280,649 A | 7/1981 | Montealegre |
| 4,301,949 A | 11/1981 | Palson et al. |
| 1,683,545 A | 9/1982 | Harris |
| 4,382,548 A | 5/1983 | van der Heijden |
| 4,391,781 A | 7/1983 | van Lit |
| 4,517,326 A | 5/1985 | Cordts et al. |
| 4,549,693 A | 10/1985 | Barlics |
| 4,594,380 A | 6/1986 | Chapin et al. |
| D286,323 S | 10/1986 | Haworth |
| 4,638,057 A | 1/1987 | Takahashi et al. |
| 4,649,046 A | 3/1987 | Kross |
| 4,703,070 A | 10/1987 | Locko et al. |
| RE32,834 E | 1/1989 | Cordts et al. |
| 4,808,347 A | 2/1989 | Dawn |
| 4,840,773 A | 6/1989 | Wade |
| 4,849,606 A | 7/1989 | Martens et al. |
| 4,874,129 A | 10/1989 | DiSapio et al. |
| 4,880,690 A | 11/1989 | Szycher et al. |
| 4,950,542 A | 8/1990 | Barker |
| 4,967,988 A | 11/1990 | Nguyen |
| 4,968,456 A | 11/1990 | Muderlak et al. |
| 5,008,115 A | 4/1991 | Lee et al. |
| 5,019,434 A | 5/1991 | Matsumoto |
| 5,034,222 A | 7/1991 | Kellett et al. |
| D319,781 S | 9/1991 | Halm et al. |
| 5,050,798 A | 9/1991 | Sullivan |
| D322,558 S | 12/1991 | Halm et al. |
| 5,071,704 A | 12/1991 | Fischel-Ghodsian |
| 5,114,625 A | 5/1992 | Gibson |
| 5,120,583 A | 6/1992 | Garcia |
| 5,178,327 A | 1/1993 | Palamand et al. |
| 5,180,107 A | 1/1993 | Lindauer |
| 5,193,445 A | 3/1993 | Fergon |
| D334,975 S | 4/1993 | Bunce |
| 5,208,027 A | 5/1993 | Weder et al. |
| 5,220,636 A | 6/1993 | Chang |
| D338,519 S | 8/1993 | Peterson |
| 5,234,162 A | 8/1993 | Sullivan |
| 5,240,487 A | 8/1993 | Kung |
| D349,157 S | 7/1994 | Rymer |
| D350,192 S | 8/1994 | Patel et al. |
| 5,368,822 A | 11/1994 | McNeil |
| 5,373,581 A | 12/1994 | Smith |
| 5,394,506 A | 2/1995 | Stein et al. |
| 5,407,642 A | 4/1995 | Lord |
| 5,422,078 A | 6/1995 | Colon |
| D367,526 S | 2/1996 | Bignon |
| D367,924 S | 3/1996 | Patel et al. |
| 5,520,921 A | 5/1996 | Chalifoux |
| D373,626 S | 9/1996 | Dente et al. |
| D375,350 S | 11/1996 | Patel et al. |
| 5,595,194 A | 1/1997 | Talbot |
| D380,258 S | 6/1997 | Muller et al. |
| 5,651,522 A | 7/1997 | Davis et al. |
| 5,683,285 A | 11/1997 | Wong |
| 5,695,692 A | 12/1997 | Kennedy |
| 5,704,832 A | 1/1998 | Borrell |
| D390,941 S | 2/1998 | Cessaroni et al. |
| D392,032 S | 3/1998 | Zaragoza et al. |
| 5,725,152 A | 3/1998 | Akyu |
| 5,762,549 A | 6/1998 | Scheuer et al. |
| 5,780,527 A | 7/1998 | O'Leary |
| 2,794,767 A | 8/1998 | Wilson |
| 5,820,791 A | 10/1998 | Canale |
| D400,662 S | 11/1998 | Davis |
| 5,845,847 A | 12/1998 | Martin et al. |
| 5,860,552 A | 1/1999 | Culhane et al. |
| 5,861,128 A | 1/1999 | Vick et al. |
| D404,957 S | 2/1999 | Cheris et al. |
| 5,871,765 A | 2/1999 | Johnson et al. |
| 5,899,382 A | 5/1999 | Hayes |
| D410,540 S | 6/1999 | Pinchuk |
| D411,002 S | 6/1999 | Farmer |
| D415,267 S | 10/1999 | Kauzlarich et al. |
| D415,268 S | 10/1999 | Farmer |
| 5,988,520 A | 11/1999 | Bitner |
| D417,727 S | 12/1999 | Christianson |
| 6,044,202 A | 3/2000 | Junkel |
| D424,677 S | 5/2000 | Chen |
| D425,190 S | 5/2000 | Morikawa |
| 6,102,660 A | 8/2000 | Lee |
| 6,104,866 A | 8/2000 | DeWitt et al. |
| 6,111,055 A | 8/2000 | Berger et al. |
| 6,123,906 A | 9/2000 | Farmer |
| 6,123,935 A | 9/2000 | Wefler et al. |
| D432,222 S | 10/2000 | Rymer et al. |
| D435,694 S | 12/2000 | Lebherz |
| D437,038 S | 1/2001 | Chuan |
| D437,041 S | 1/2001 | Eisenbraun |
| 6,190,607 B1 | 2/2001 | Farmer |
| 6,191,197 B1 | 2/2001 | Wang et al. |
| 6,197,263 B1 | 3/2001 | Blount |
| 6,202,938 B1 | 3/2001 | Collier |
| D440,294 S | 4/2001 | Bilek |
| D441,441 S | 5/2001 | Upson |
| 6,241,161 B1 * | 6/2001 | Corbett ............... 239/58 |
| 6,264,887 B1 | 7/2001 | Farmer |
| 6,291,371 B1 | 9/2001 | Shefer et al. |
| 6,309,715 B1 | 10/2001 | Lindauer et al. |
| 6,325,475 B1 | 12/2001 | Hayes et al. |
| D454,190 S | 3/2002 | Trocola |
| 6,357,260 B1 | 3/2002 | Lutz |
| 6,374,044 B1 | 4/2002 | Freidel |
| 6,375,966 B1 | 4/2002 | Maleeny et al. |
| 6,379,689 B1 | 4/2002 | Aguadisch |
| 6,391,398 B1 | 5/2002 | Pesu et al. |
| 6,416,043 B1 | 7/2002 | Elsenbraun |
| 6,514,467 B1 | 2/2003 | Bulsink et al. |
| D472,968 S | 4/2003 | Christianson |
| D478,379 S | 8/2003 | Talenton et al. |
| D478,973 S | 8/2003 | Wagner |
| 6,609,935 B2 | 8/2003 | Huang |
| D479,592 S | 9/2003 | Lammel et al. |
| D485,343 S | 1/2004 | Wu |
| D487,504 S | 3/2004 | Yuen |
| 6,712,286 B2 | 3/2004 | Baxter et al. |
| D488,214 S | 4/2004 | Quantin |
| D488,548 S | 4/2004 | Lablaine |
| D491,257 S | 6/2004 | Picken |
| D491,798 S | 6/2004 | Buthier |
| D496,720 S | 9/2004 | Dudley |
| 6,800,252 B1 | 10/2004 | Jedzinski |
| 6,830,733 B2 | 12/2004 | Stanley, III |
| 6,885,811 B2 | 4/2005 | He et al. |
| D504,943 S | 5/2005 | Dudley |
| D507,341 S | 7/2005 | Taylor |
| D511,568 S | 11/2005 | Wheatley |
| D514,679 S | 2/2006 | Wheatley |
| D515,192 S | 2/2006 | Smith et al. |
| 7,025,283 B2 | 4/2006 | Torres |
| 7,055,764 B1 | 6/2006 | Martinez et al. |
| 7,061,386 B2 | 6/2006 | Seresini |
| 7,070,172 B2 | 7/2006 | Fabrega et al. |
| 7,137,570 B2 | 11/2006 | Wheatley et al. |
| 7,141,215 B2 | 11/2006 | Guan et al. |
| D535,376 S | 1/2007 | Michaels et al. |
| D535,379 S | 1/2007 | Hundertmark |
| 7,159,792 B2 | 1/2007 | Wheatley et al. |
| D544,080 S | 6/2007 | Carlson |
| D544,084 S | 6/2007 | Michaels et al. |
| D544,594 S | 6/2007 | Zobele |
| D544,953 S | 6/2007 | Kee |
| D546,432 S | 7/2007 | Hundertmark |
| 7,243,859 B2 | 7/2007 | Caserta et al. |
| D548,317 S | 8/2007 | Newton et al. |

(56) References Cited

U.S. PATENT DOCUMENTS

| | | | |
|---|---|---|---|
| D550,345 | S | 9/2007 | Weggelaar |
| D551,333 | S | 9/2007 | Wu |
| D554,746 | S | 11/2007 | Davis et al. |
| 7,293,719 | B2 | 11/2007 | Wheatley |
| D565,162 | S | 3/2008 | Carlson |
| 7,344,123 | B2 | 3/2008 | Pankhurst et al. |
| D565,715 | S | 4/2008 | Wu |
| D573,706 | S | 7/2008 | Zlotnik et al. |
| D574,941 | S | 8/2008 | Weggelaar |
| 7,441,360 | B2 | 10/2008 | Christianson et al. |
| D580,039 | S | 11/2008 | Zlotnik et al. |
| D585,129 | S | 1/2009 | Huang |
| D585,971 | S | 2/2009 | Carrizales |
| D591,415 | S | 4/2009 | Wu |
| D593,670 | S | 6/2009 | Valentino et al. |
| D594,953 | S | 6/2009 | King et al. |
| D594,954 | S | 6/2009 | Wheatley |
| 7,544,331 | B1 | 6/2009 | Pettaway |
| 7,544,332 | B2 | 6/2009 | De Silva et al. |
| D597,645 | S | 8/2009 | Thompson |
| D598,531 | S | 8/2009 | Irvin |
| D604,825 | S | 11/2009 | Brandenburg |
| D607,983 | S | 1/2010 | Irvin |
| 7,651,666 | B2 | 1/2010 | Adair et al. |
| 7,670,566 | B2 | 3/2010 | Adair et al. |
| 7,687,037 | B2 | 3/2010 | Wheatley |
| 7,687,038 | B2 | 3/2010 | Wheatley |
| D614,277 | S | 4/2010 | Hsiao |
| D619,692 | S | 7/2010 | Hami et al. |
| D619,693 | S | 7/2010 | Hami et al. |
| D619,694 | S | 7/2010 | Hami et al. |
| D620,573 | S | 7/2010 | Hami et al. |
| D622,835 | S | 8/2010 | Mendheim |
| 7,780,094 | B2 | 8/2010 | Caserta et al. |
| D625,798 | S | 10/2010 | Hami et al. |
| D629,881 | S | 12/2010 | Valentino et al. |
| D631,534 | S | 1/2011 | Kajizuka |
| D631,954 | S | 2/2011 | Bertassi et al. |
| D633,610 | S | 3/2011 | Wu |
| D637,275 | S | 5/2011 | Baraky |
| D640,358 | S | 6/2011 | Irvin |
| D640,781 | S | 6/2011 | Brandenburg |
| D642,668 | S | 8/2011 | Lablaine |
| D645,949 | S | 9/2011 | Brandenburg et al. |
| D647,186 | S | 10/2011 | Chan et al. |
| D649,237 | S | 11/2011 | Bilko et al. |
| D650,892 | S | 12/2011 | Wheatley |
| 8,090,244 | B2 | 1/2012 | Belongia et al. |
| 8,147,761 | B2 | 4/2012 | Wheatley et al. |
| D660,950 | S | 5/2012 | Finlay |
| D662,581 | S | 6/2012 | Savegnago |
| 8,197,761 | B1 | 6/2012 | Miller-Larry |
| 8,251,299 | B1 | 8/2012 | Irvin |
| D667,100 | S | 9/2012 | Harkim |
| 8,460,609 | B1 | 6/2013 | Wheatley et al. |
| 8,480,960 | B2 | 7/2013 | Wheatley et al. |
| 8,485,454 | B1 | 7/2013 | Irvin |
| 8,490,846 | B1 | 7/2013 | Wheatley |
| 2001/0051234 | A1 | 12/2001 | Ryan et al. |
| 2003/0097936 | A1 | 5/2003 | Maleeny et al. |
| 2003/0199421 | A1 | 10/2003 | Copfer |
| 2004/0197221 | A1 | 10/2004 | Stanley, III |
| 2004/0265164 | A1 | 12/2004 | Woo et al. |
| 2005/0084413 | A1 | 4/2005 | Stanley, III |
| 2005/0127538 | A1 | 6/2005 | Fabrega et al. |
| 2005/0169793 | A1 | 8/2005 | Wheatley et al. |
| 2006/0043216 | A1 | 3/2006 | Robinson |
| 2006/0078477 | A1 | 4/2006 | Althoe et al. |
| 2006/0196964 | A1 | 9/2006 | Wheatley et al. |
| 2006/0279008 | A1 | 12/2006 | Jursich |
| 2007/0057084 | A1 | 3/2007 | Vieira |
| 2007/0160492 | A1 | 7/2007 | Spector |
| 2007/0231508 | A1 | 10/2007 | Fand et al. |
| 2007/0290064 | A1 | 12/2007 | Majerowski et al. |
| 2008/0099576 | A1 | 5/2008 | Hart |
| 2008/0128925 | A1 | 6/2008 | Pankhurst et al. |
| 2008/0311315 | A1 | 12/2008 | Marlow |
| 2008/0311316 | A1 | 12/2008 | Marlow |
| 2009/0004420 | A1 | 1/2009 | Wheatley |
| 2009/0010813 | A1 | 1/2009 | Wang et al. |
| 2009/0072045 | A1 | 3/2009 | Wheatley et al. |
| 2009/0148142 | A1 | 6/2009 | McGee et al. |
| 2009/0173799 | A1 | 7/2009 | Litten-Brown et al. |
| 2009/0196587 | A1 | 8/2009 | Cheung |
| 2010/0010409 | A1 | 1/2010 | Irvin |
| 2010/0019059 | A1 | 1/2010 | Bulsink et al. |
| 2010/0065654 | A1 | 3/2010 | Wheatley et al. |
| 2010/0187327 | A1 | 7/2010 | Irvin |
| 2010/0288847 | A1 | 11/2010 | Gruenbacher et al. |
| 2011/0108632 | A1 | 5/2011 | Brandenburg et al. |
| 2011/0110823 | A1 | 5/2011 | Wheatley et al. |
| 2012/0076276 | A1 | 3/2012 | Wang et al. |

FOREIGN PATENT DOCUMENTS

| | | |
|---|---|---|
| EP | 1 346 734 | 9/2003 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2004/078219 | 9/2004 |
| WO | WO 2006/010282 | 2/2006 |
| WO | WO 2006/084160 | 8/2006 |

OTHER PUBLICATIONS

U.S. Appl. No. 12/979,690, filed Dec. 28, 2010; Alan J. Wheatley; office action dated Mar. 1, 2013.

U.S. Appl. No. 12/987,662, filed Jan. 10, 2011; Alan J. Wheatley; office action dated Mar. 21, 2013.

U.S. Appl. No. 12/979,601, filed Dec. 28, 2010; Alan J. Wheatley; office action dated Mar. 1, 2013.

U.S. Appl. No. 13/009,574, filed Jan. 19, 2011; Alan J. Wheatley notice of allowance dated Apr. 3, 2013.

U.S. Appl. No. 13/359,726, filed Jan. 27, 2012; Aaron Irvin; office action dated Apr. 5, 2013.

U.S. Appl. No. 12/979,763, filed Dec. 28, 2010; Aaron Irvin notice of allowance dated Apr. 15, 2013.

U.S. Appl. No. 13/282,035, filed Oct. 26, 2011; Nathaniel Finlay, office action dated Apr. 17, 2013.

U.S. Appl. No. 12/987,662, filed Jan. 10, 2011; Alan J. Wheatley; notice of allowance dated Jun. 7, 2013.

U.S. Appl. No. 12/979,690, filed Dec. 28, 2010; Alan J. Wheatley; notice of allowance dated Jun. 10, 2013.

U.S. Appl. No. 12/979,601, filed Dec. 28, 2010; Alan J. Wheatley; notice of allowance dated Jun. 10, 2013.

U.S. Appl. No. 29/435,391, filed Oct. 23, 2012; Aaron Irvin, notice of allowance dated Jun. 18, 2013.

U.S. Appl. No. 13/282,035, filed Oct. 26, 2011; Nathaniel Finlay; office action dated Jul. 17, 2013.

U.S. Appl. No. 12/979,795, filed Dec. 28, 2010; Aaron Irvin; office action dated Oct. 18, 2013.

U.S. Appl. No. 13/940,074, filed Jul. 11, 2013; Alan J. Wheatley; office action dated Nov. 20, 2013.

U.S. Appl. No. 12/915,924, filed Oct. 29, 2010; Nathaniel Finlay; notice of allowance dated Nov. 22, 2013.

U.S. Appl. No. 13/282,035, filed Oct. 26, 2011; Nathaniel Finlay; notice of allowance dated Nov. 26, 2013.

U.S. Appl. No. 13/281,890, filed Oct. 26, 2011; Aaron Irvin; notice of allowance dated Dec. 10, 2013.

About.com Housekeeping, http://housekeeping.about.com/od/pr . . . affresh, Febrezee Noticeables, accessed Oct. 2, 2008, 2 pages.

Aromate E-News, Innovation in Novelty Fragrance, Http://209.85. 173.104/seasrch?qcach . . . , accessed Oct. 8, 2008, 2 pages.

Ecrater, www.ecrater.com/product.hp? . . . , Yankee Candle Selects Two Scents Electric Fragrance Unit Macintosh/Home Sweet Home, accessed Oct. 2, 2008, 1 page.

http://decomodo.com/articles/categor/lighting/, Bamboo Pillar Candle, Jan. 8, 2008, 1 page.

(56) References Cited

OTHER PUBLICATIONS http://shop.advanceautoparts.com/webapp/wcs/stores/servlet/product_6170795-P_N3004 . . . Advance Auto Part; Arometrics Dual-Scent Vent—Juicy Strawberry and Vanilla; 1 Page; accessed Dec. 10, 2010.

http://www.bestliquidations.com/Medo_Vent Frehser.htm; BestLiquidations.com; Medo Vent Fresh Air Fresheners; 2 pages; accessed Dec. 10, 2010.

Medo® Air Fresheners; Auto Expressions™ 2005 Product Catalog; 25 pages.

Pictures (3) of Medo® auto Expressions Vent™ Air Freshener distributed by SOPUS Products of Moorpark , CA 2003 copyright date on package.

Scents & Sprays, www.scentsandsprays.com/ya . . . , Yankee Autumn Bounty Electric 2 Home Air Fresheners, copyright 2001-2008 scentsandsprays.com, accessed Oct. 2, 2008, 1 page.

www.4imprint.com/EXEC/DETAIL/FROMPRODUCT-GROUP/~SKU100300/~CA100300.htm, Hot Rod Vent Stick Air Freshener (it . . . , accessed Aug. 12, 2008, 2 pages.

www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.

www.chicscents.com/Products.aspx Island Adventure Sandals; 2 pages; accessed Feb. 1, 2011.

www.chicscents.com/Products.aspx; Inspiration 3-D by Chic; 2 pages; accessed Feb. 1, 2011.

U.S. Appl. No. 12/979,763, filed Dec. 28, 2010; Aaron Irvin.

U.S. Appl. No. 12/979,795, filed Dec. 28, 2010; Aaron Irvin.

U.S. Appl. No. 12/979,813, filed Dec. 28, 2010; Aaron Irvin.

U.S. Appl. No. 13/191,966, filed Jul. 27, 2011; Aaron Irvin.

U.S. Appl. No. 12/979,763, filed Dec. 28, 2010; Aaron Irvin; office action dated Dec. 14, 2012.

U.S. Appl. No. 12/693,543, filed Jan. 26, 2010; Aaron Irvin; office action dated Dec. 18, 2012.

U.S. Appl. No. 13/009,574, filed Jan. 19, 2011; Alan J. Wheatley; office action dated Jan. 11, 2013.

U.S. Appl. No. 12/979,795, filed Dec. 28, 2010; Aaron Irvin; office action dated Jan. 28, 2013.

U.S. Appl. No. 12/979,813, filed Dec. 28, 2010; Aaron Irvin; office action dated Jan. 31, 2013.

U.S. Appl. No. 12/915,983, filed Oct. 29, 2010; Alan J. Wheatley; notice of allowance dated Feb. 20, 2013.

\* cited by examiner

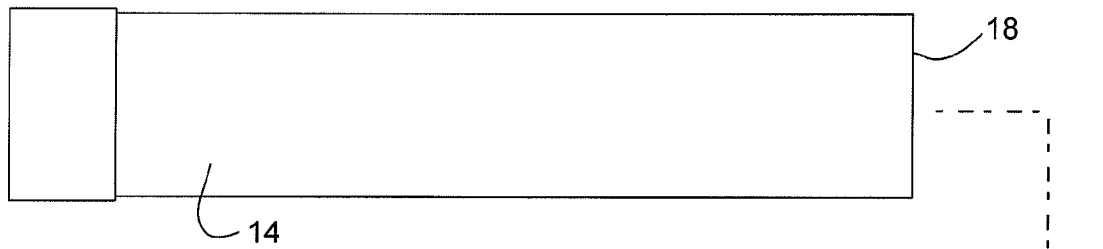
Fig. 1c
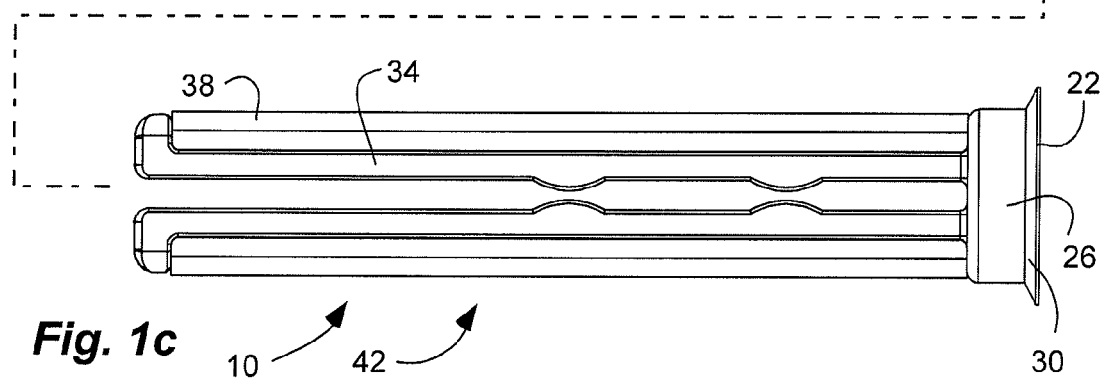
Fig. 2
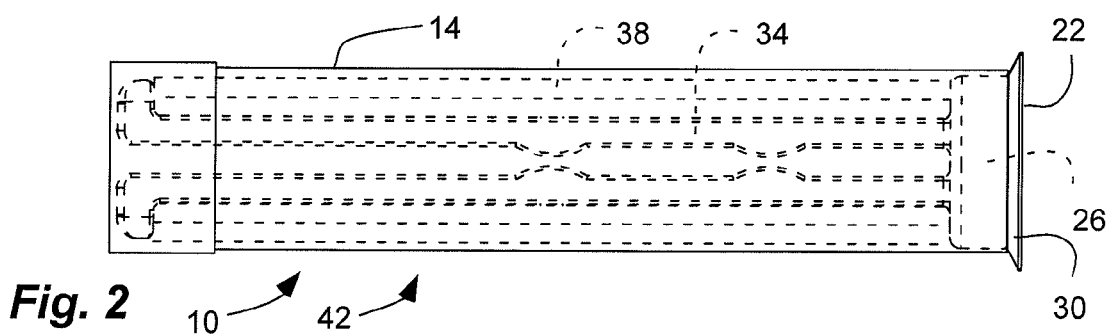
Fig. 3
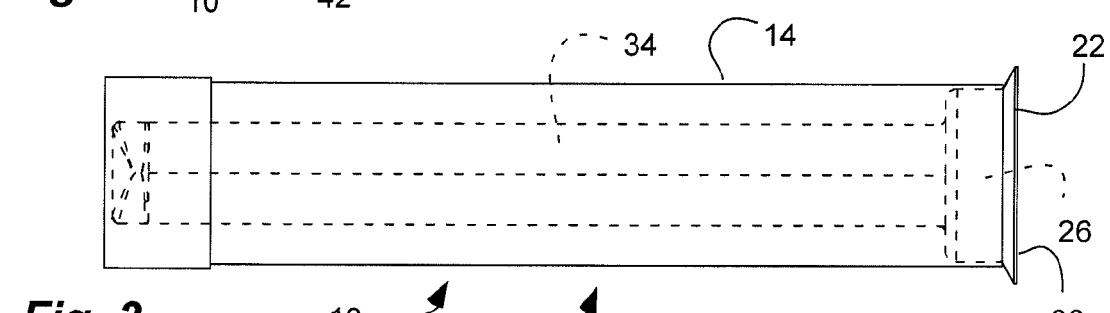
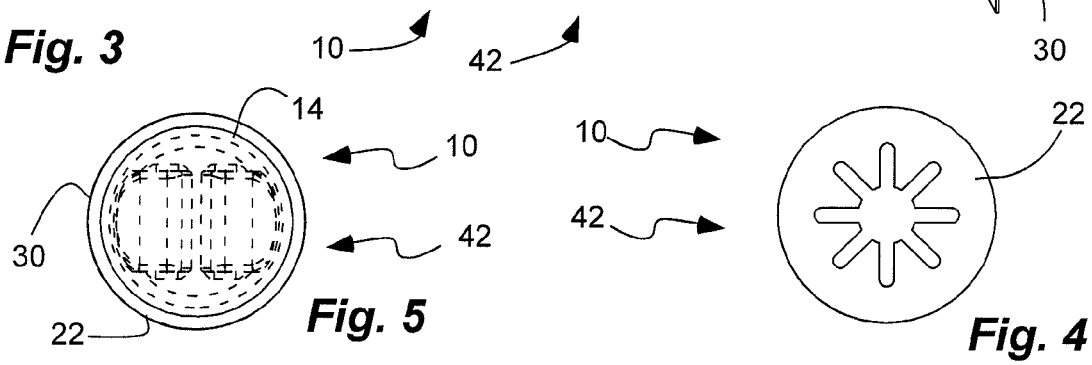
Fig. 5
Fig. 4

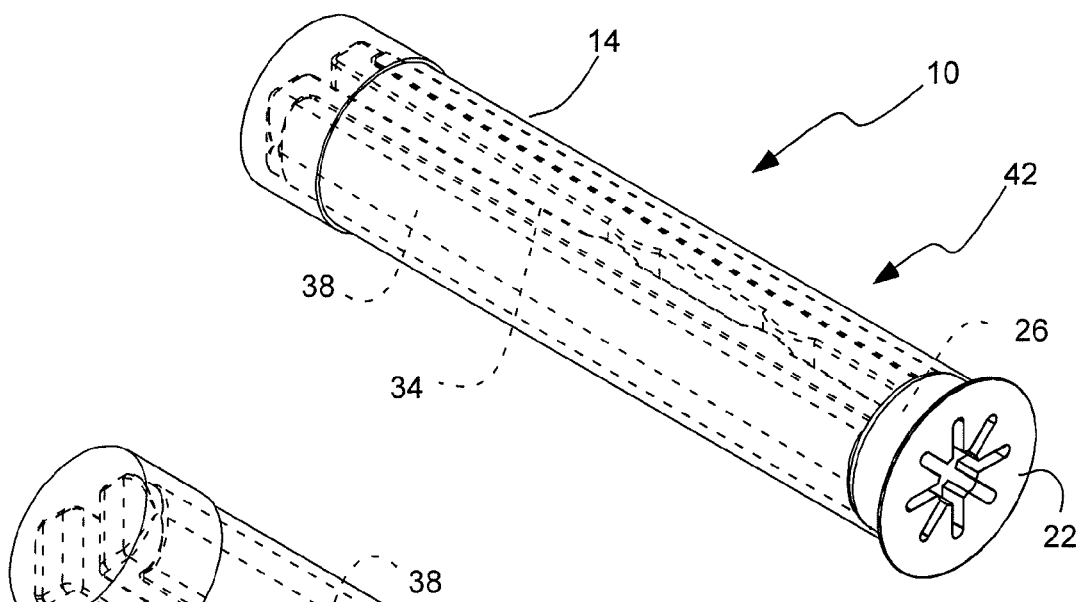
*Fig. 6a*
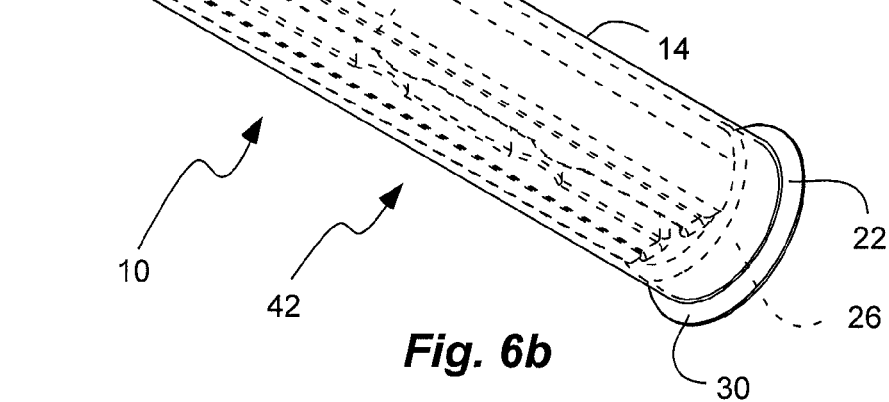
*Fig. 6b*
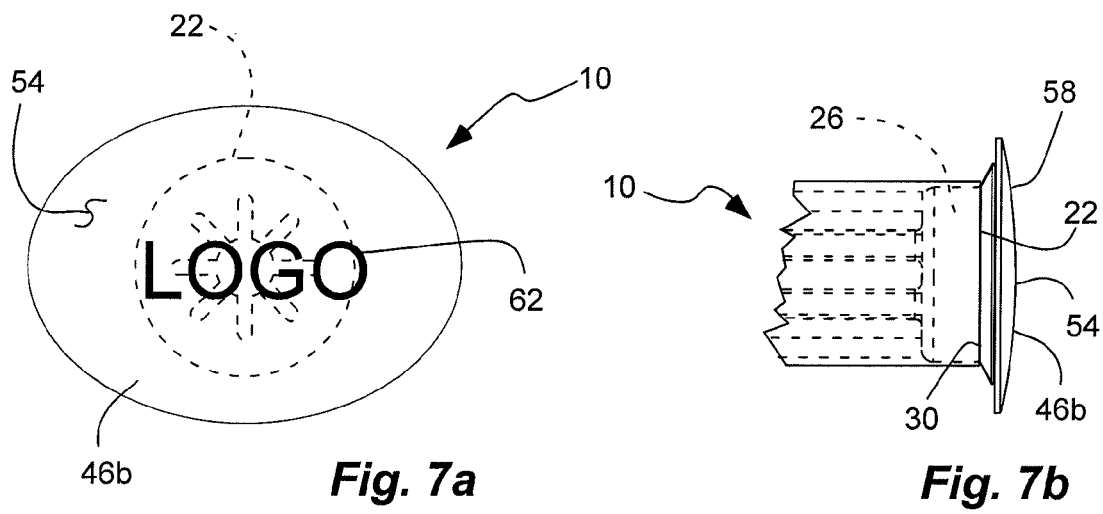
*Fig. 7a*      *Fig. 7b*

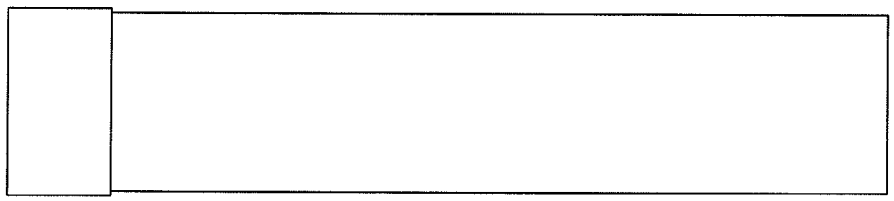
Fig. 9a
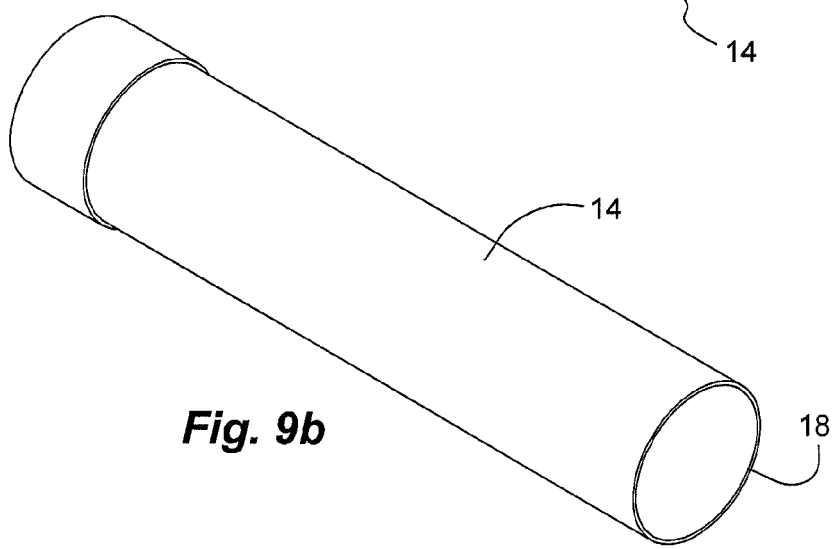
Fig. 9b
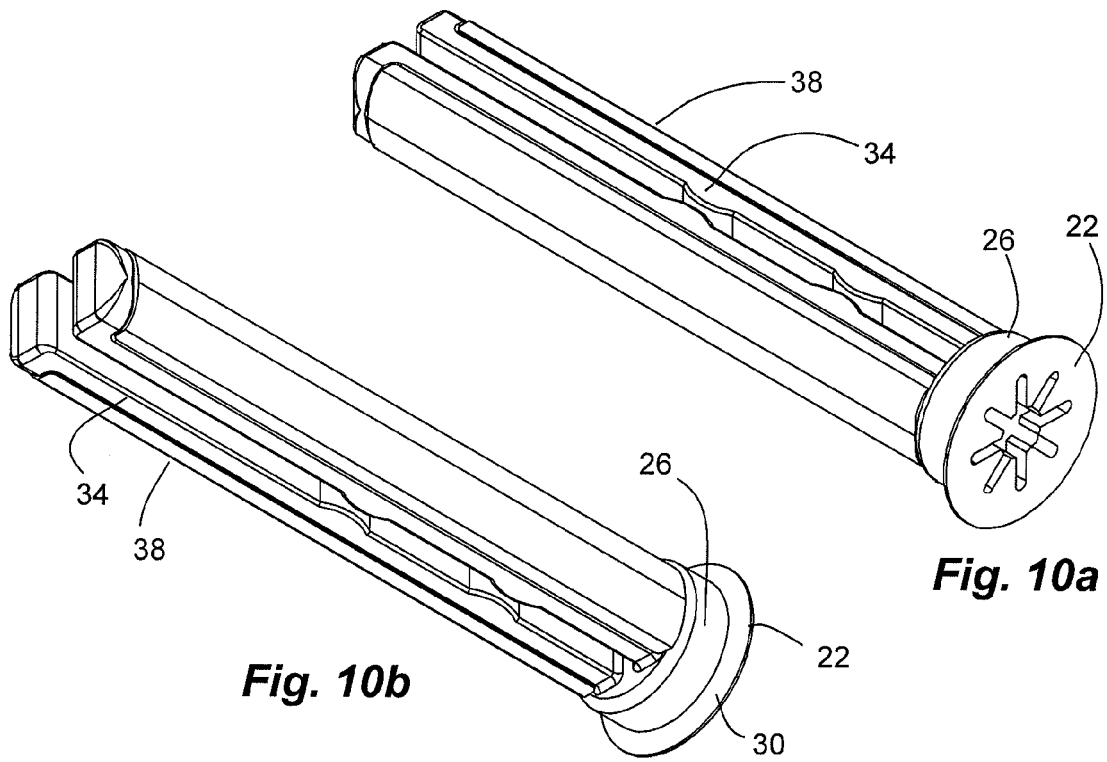
Fig. 10a
Fig. 10b

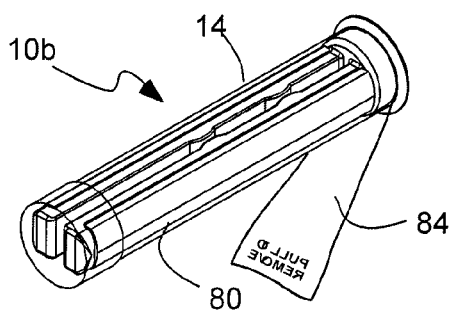
Fig. 16a
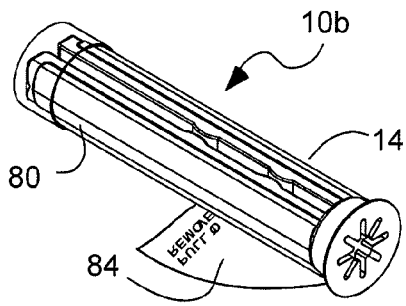
Fig. 16b
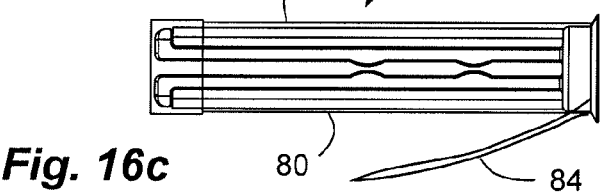
Fig. 16c
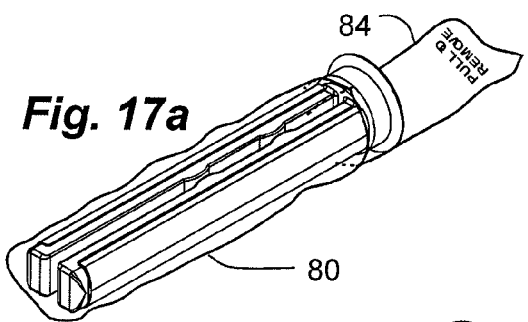
Fig. 17a
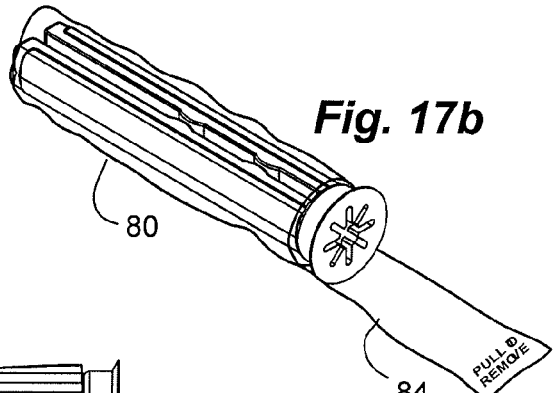
Fig. 17b
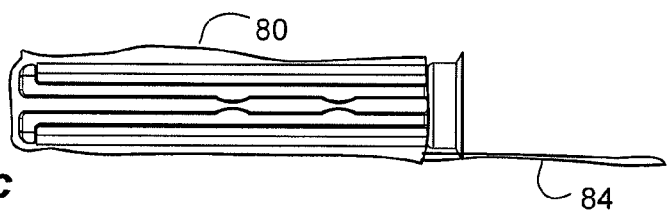
Fig. 17c
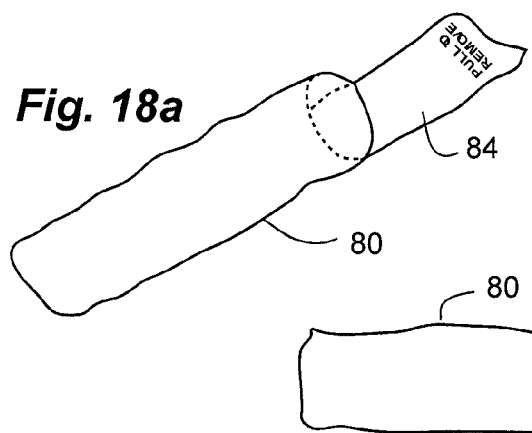
Fig. 18a
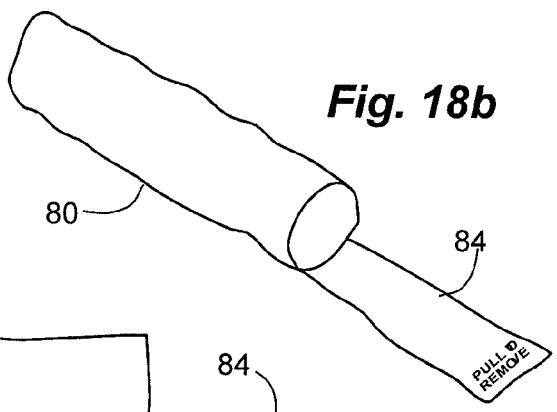
Fig. 18b
Fig. 18c

PACKAGED VENT STICK AIR FRESHENER WITH CUSTOM HEAD

PRIORITY CLAIM

Priority is claims to U.S. Provisional Patent Application Ser. No. 61/566,161, filed Dec. 2, 2011, and which is hereby incorporated herein by reference.

RELATED APPLICATIONS

This is related to U.S. Pat. Nos. 7,137,570; 7,293,719; 7,687,038; 7,687,037; and 7,159,792; and U.S. patent application Ser. No. 13/009,574, filed Jan. 19, 2011; and Ser. No. 12/623,007, filed Nov. 20, 2009; which are hereby incorporated herein by reference in their entirety.

BACKGROUND

1. Field of the Invention

The present invention relates generally to vent stick air fresheners.

2. Related Art

Various types of air fresheners have been proposed.

SUMMARY OF THE INVENTION

It has been recognized that it would be advantageous to develop an air freshener blank capable of receiving a custom head while the air freshener blank is packaged.

The invention provides an air freshener with a container having an open end. A sub-head has a back with at least a portion of the sub-head releasably coupled across the open end of the container and closing the container. The sub-head also has a front with the front of the sub-head exposed. A vent rod extends from the back of the sub-head and into the container. The vent rod is configured to be inserted through an air vent to the sub-head when the container is removed from the sub-head. A scent material has a desired scent carried by the vent rod, and extends into the container with the vent rod, and is contained in the container by the sub-head. The scent material is insertable through the air vent with the vent rod when the container is removed from the sub-head. A supra-head with a back is coupled to the front of the sub-head. The supra-head has a front with a face, and a lateral dimension larger than a lateral dimension of the sub-head and covering the sub-head.

In addition, the invention provides an air freshener with a tube having a substantially cylindrical wall with an open substantially circular end. The tube also has a closed end. The cylindrical wall is at least translucent. A sub-head has a back with a substantially circular rear disc removably inserted into the open substantially circular end of the tube, closing the tube. The sub-head has a front with an enlarged front side extending laterally beyond the rear disc. A pair of vent rods extends from the back of the sub-head and into the tube. The pair of vent rods form a clip configured to be inserted through and engage an air vent when the tube is removed from the sub-head. A pair of scented bodies has a scent material with a desired scent. Each scented body is sized similarly to a vent rod, and each is carried by a different one of the pair of vent rods, and extends into the tube with the pair of vent rods and contained in the tube. Each body is insertable through the air vent with the pair of vent rods when the tube is removed from the sub-head. A bag extends around the pair of scented bodies and the pair of vent rods with a bag opening substantially concentric with the open end of the tube. The bag has a tab extending out of the container between the open end of the tube and the rear disc of the sub-head. The tube, the sub-head, the pair of vent rods and the pair of scented bodies define an air freshener blank capable of receiving one of a plurality of different supra-heads. The one of a plurality of different supra-heads has a back affixed to the front of the sub-head and has a front with a face. The supra-head is sized larger than the sub-head, and covers the sub-head. The supra-head is disposed outside of the tube.

Furthermore, the invention provides a method for providing custom air fresheners that includes obtaining a plurality of air freshener blanks. Each blank includes a container having an open end; a sub-head having a back with at least a portion of the sub-head releasably coupled across the open end of the container and closing the container, and having a front with the front of the sub-head exposed; a vent rod extending from the back of the sub-head and into the container; and a scent material having a desired scent carried by the vent rod and extending into the container with the vent rod and contained in the container by the sub-head. A plurality of custom supra-heads is obtained. Each supra-head comprises a back and a front with a face. The supra-head has a lateral dimension larger than a lateral dimension of the sub-head. affixing the plurality of custom supra-heads to the sub-heads of the plurality of blanks and covering the sub-heads.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 1c is a side view of the air freshener blank of FIG. 1a, shown with the air freshener removed from the container or tube;

FIG. 2 is a side view of the air freshener blank of FIG. 1a, without the custom supra-head;

FIG. 3 is a top view of the air freshener blank of FIG. 1a, without the custom supra-head;

FIG. 4 is a front end view of the air freshener blank of FIG. 1a, without the custom supra-head;

FIG. 5 is a rear end view of the air freshener blank of FIG. 1a, without the custom supra-head;

FIG. 6a is a front perspective view of the air freshener blank of FIG. 1a, without the custom supra-head;

FIG. 6b is a rear perspective view of the air freshener blank of FIG. 1a, without the custom supra-head;

FIG. 7a is a front view of the air freshener blank of FIG. 1a, with the custom supra-head;

FIG. 7b is a partial side view of the air freshener blank of FIG. 1a, with the custom supra-head;

FIG. 9a is a side view of the container or tube of the air freshener blank of FIG. 1a, with the air freshener removed;

FIG. 9b is a front perspective view of the container or tube of the air freshener blank of FIG. 1a, with the air freshener removed;

FIG. 10a is a front perspective view of the air freshener of the air freshener blank of FIG. 1a, without the tube or container and without the custom supra-head;

FIG. 10b is a rear perspective view of the air freshener of the air freshener blank of FIG. 1a, without the tube or container and without the custom supra-head;

FIGS. 15a-d are front views of a plurality of custom supra-heads of the air freshener blank of FIG. 1a;

FIG. 16a is a rear perspective view of another air freshener blank with a vent-style air freshener in accordance with an embodiment of the present invention without a custom supra-head, and with a sleeve between vent rods of the air freshener and the tube or container;

FIG. 16b is a front perspective view of the air freshener blank of FIG. 16a without a custom supra-head, and with a sleeve or bag between vent rods of the air freshener and the tube or container;

FIG. 16c is a side view of the air freshener blank of FIG. 16a without a custom-supra head, and with a sleeve or bag between vent rods of the air freshener and the tube or container;

FIG. 17a is a rear perspective view of the sleeve or bag with the air freshener of FIG. 16a removed from the tube or container, and without the custom supra-head;

FIG. 17b is a front perspective view of the sleeve or bag with the air freshener of FIG. 16a removed from the tube or container, and without the custom supra-head;

FIG. 17c is a side view of the sleeve or bag with the air freshener of FIG. 16a removed from the tube or container, and without the custom supra-head;

FIG. 18a is a rear perspective view of the sleeve or bag of the air freshener blank of FIG. 16a removed from the tube or container and with the air freshener removed therefrom;

FIG. 18b is a front perspective view of the sleeve or bag of the air freshener blank of FIG. 16a removed from the tube or container and with the air freshener removed therefrom; and FIG. 18c is a side view of the sleeve or bag of the air freshener blank of FIG. 16a removed from the tube or container and with the air freshener removed therefrom.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The terms "packaging" and "container" and "tube" are used interchangeably throughout.

The terms "custom head" and "supra-head" are used interchangeably herein.

The terms "air freshener" and "air freshener blank" and "blank" are used interchangeably throughout. In addition, the term "air freshener" is used herein to refer to the operational portion of the air freshener that is utilized in an air vent, and with the supra-head or custom head or custom supra-head affixed thereto. Furthermore, the term "air freshener" is used herein to refer to the air freshener blank with the supra-head or custom head or custom supra-head affixed thereto. The terms "air freshener blank" and "blank" are used to refer to the air freshener packaged, but without a supra-head or custom head or custom supra-head.

The terms "scent" and "scent material" are used to refer to a desired fragrance, such as flowers, fruits, etc., but also is used broadly to refer to a neutralizing agent.

Description

Figure 1A:
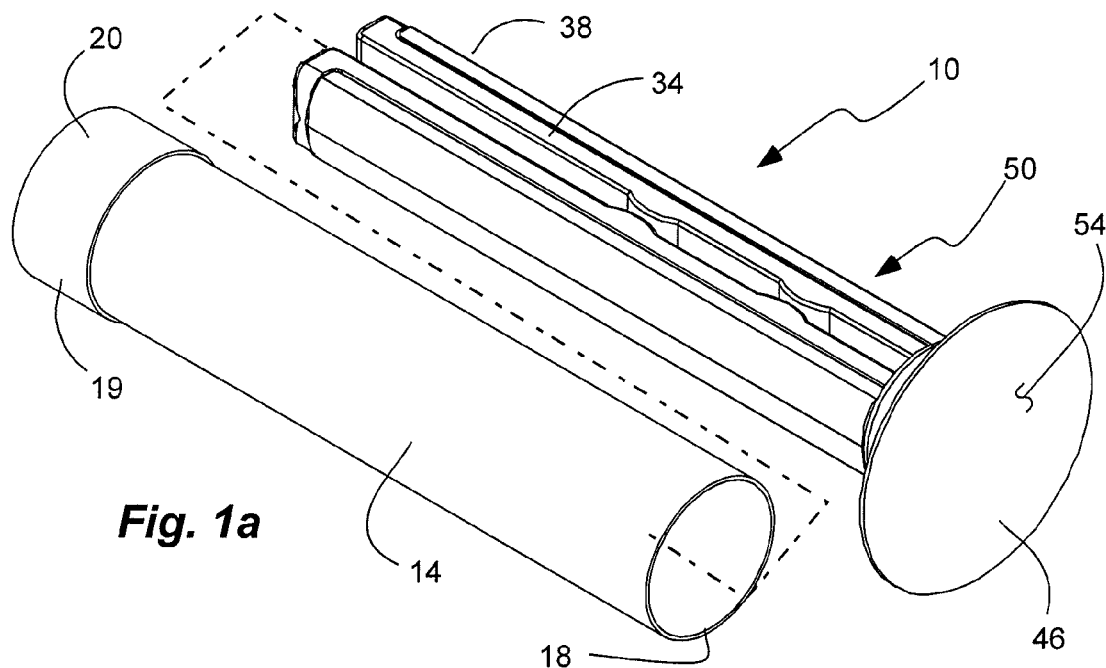
FIG. 1a is a front perspective view of an air freshener blank with a vent-style air freshener with a custom supra-head, shown with the air freshener removed from a container or tube, in accordance with an embodiment of the present invention.
Figure 1B:
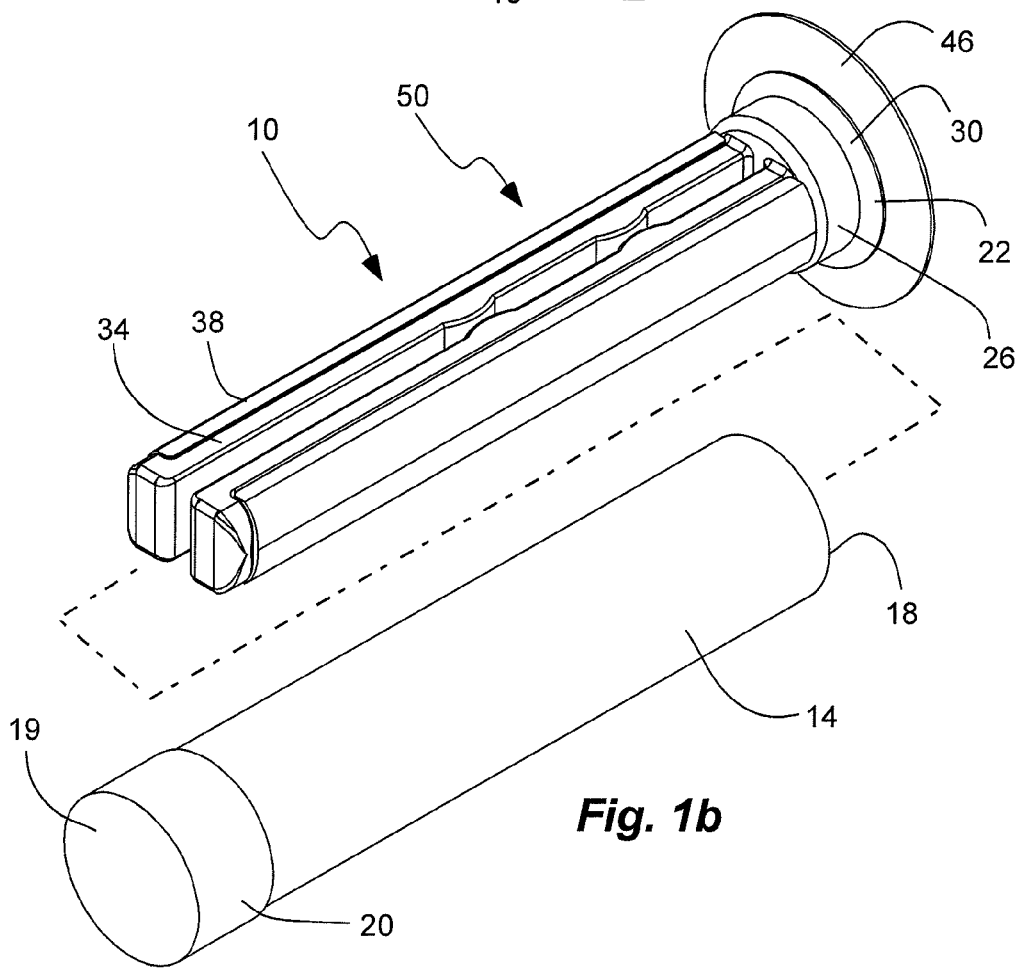
FIG. 1b is a rear perspective view of the air freshener blank of FIG. 1a, shown with the air freshener removed from the container or tube.
Figure 8A:
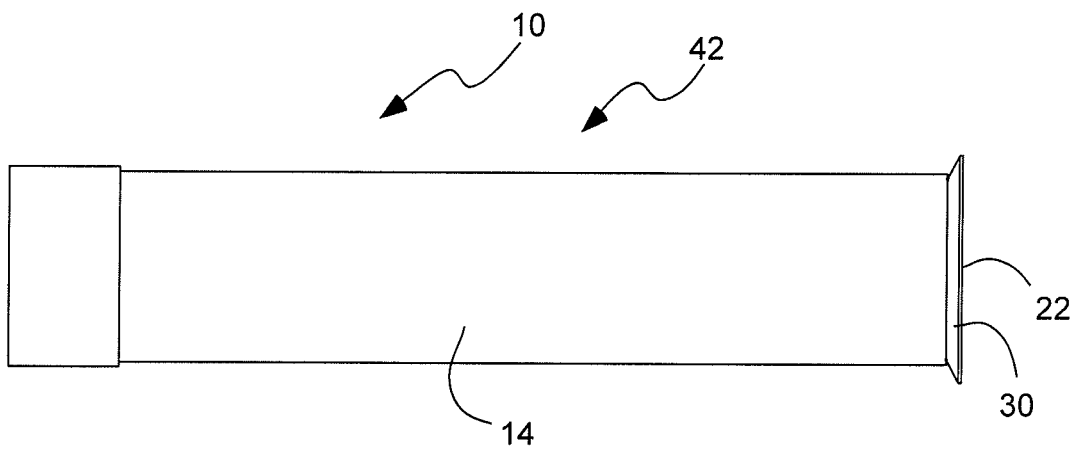
FIG. 8a is a side view of the air freshener blank of FIG. 1a, without the custom supra-head.
Figure 8B:
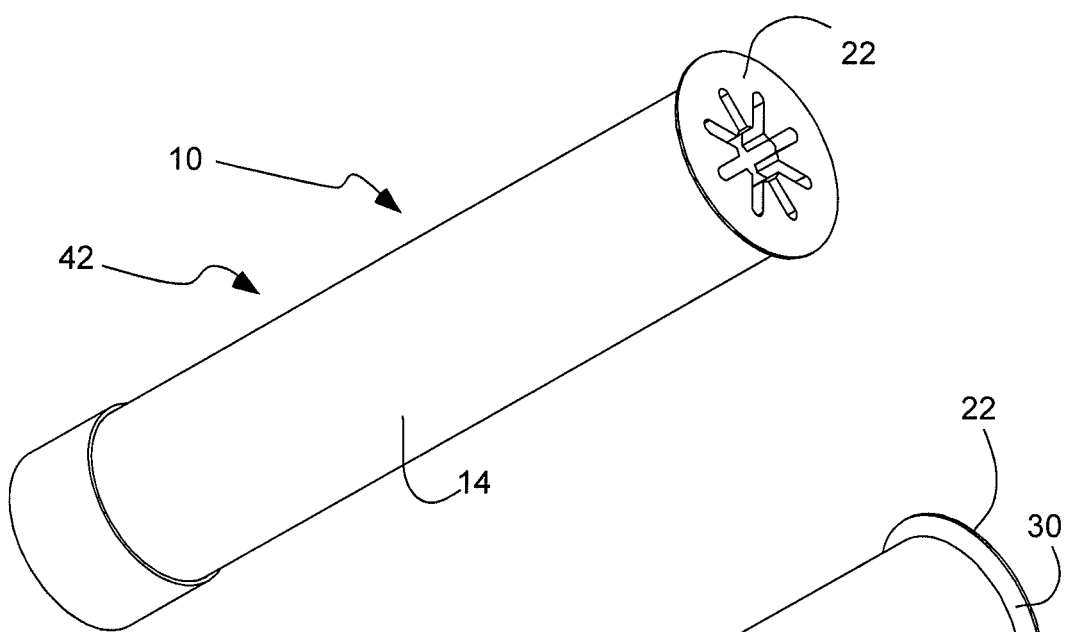
FIG. 8b is a front perspective view of the air freshener blank of FIG. 1a, without the custom supra-head.
Figure 8C:
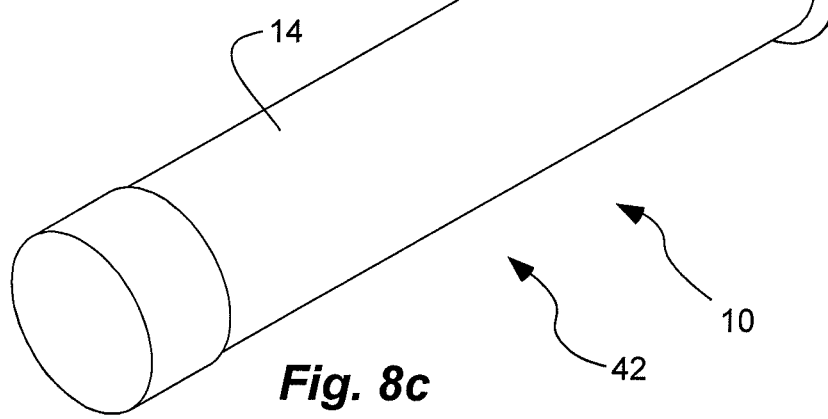
FIG. 8c is a rear perspective view of the air freshener blank of FIG. 1a, without the custom supra-head.
Figure 11:
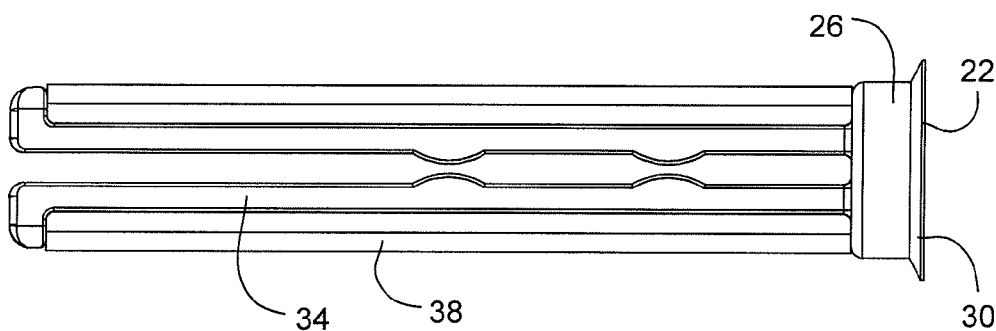
FIG. 11 is a side view of the air freshener of the air freshener blank of FIG. 1a, without the tube or container and without the custom supra-head.
Figure 12:
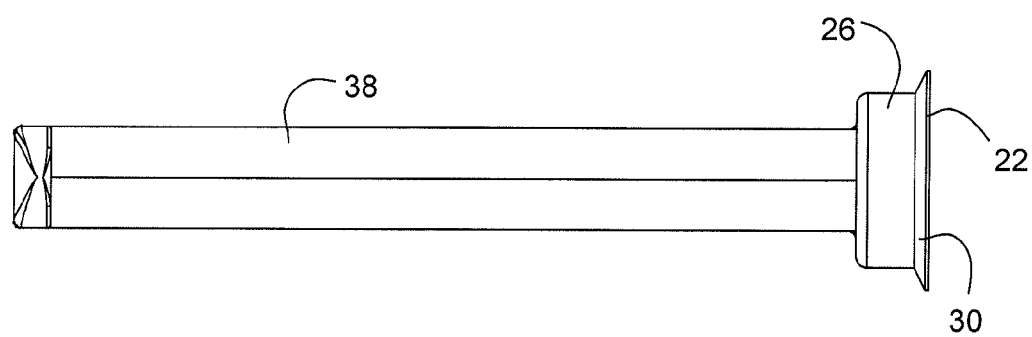
FIG. 12 is a top view of the air freshener of the air freshener blank of FIG. 1a, without the tube or container and without the custom supra-head.
Figure 14:
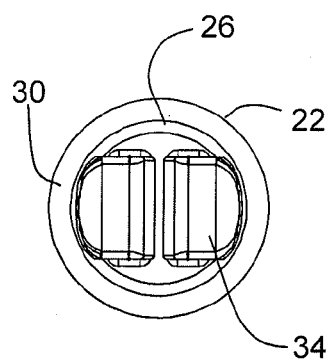
FIG. 14 is a rear end view of the air freshener of the air freshener blank of FIG. 1a, without the tube or container and without the custom supra-head.
Figure 13:
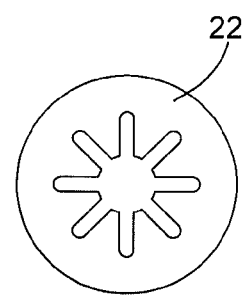
FIG. 13 is a front end view of the air freshener of the air freshener blank of FIG. 1a, without the tube or container and without the custom supra-head.
Figure 15A:
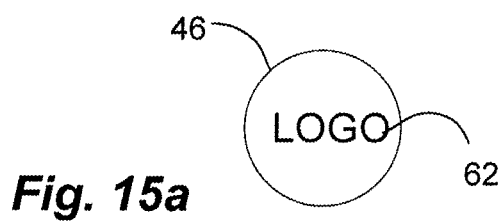
Figure 15B:
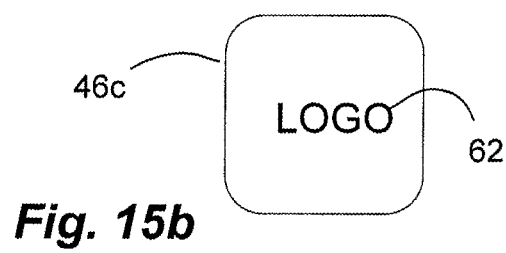
Figure 15C:
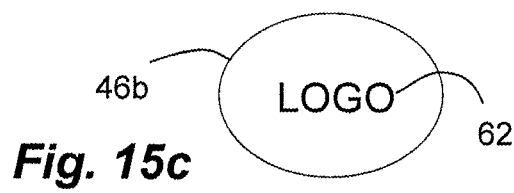
Figure 15D:
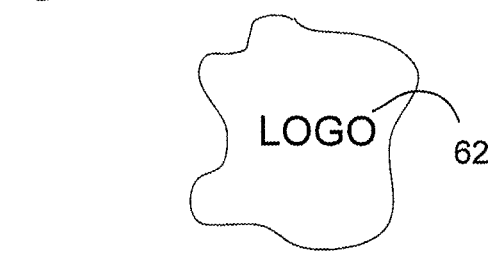

As illustrated in FIGS. 1a-15, an air freshener device or air freshener blank, indicated generally at 10, in an example implementation in accordance with the invention is shown. The air freshener or blank 10 includes a packaging in which at least a portion of the head of the air freshener or blank is removably coupled to and closes the packaging. In addition, a plurality of such blanks can be provided to receive different custom supra-heads. Thus, custom air fresheners can be provided using prefabricated and prepackaged air freshener blanks. The custom supra-heads can be affixed to an exposed (through the packaging) portion of a sub-head; with the sub-head being removably coupled to and closing the packaging. The blanks can be fabricated in bulk quantities, and smaller lots finished at different times with different custom supra-heads that can be fabricated later.

The air freshener or blank 10 can include a container or tube 14 with an open end 18 and a closed end 19. The container or tube 14 can have a substantially cylindrical wall and the open end can be substantially circular. The container or tube can define a hollow therein. The cylindrical wall can be at least translucent, and even transparent or clear, to allow visibility of the air freshener and/or scented bodies therein. The container or tube can be elongated and can have a diameter or lateral side less than a longitudinal length. The container or tube can be formed by an extruded plastic tube or cylinder, with the closed end formed by a plastic cap 20 affixed to the end with adhesive, sonic welding, or the like.

In addition, the air freshener or blank 10 can includes a sub-head 22 having a back and a front. The sub-head 22 can have a substantially circular rear disc 26 removably insertable into the open end 18 of the container or tube 14 and closing the container or tube. Thus, the container or tube and the sub-head, or rear disc thereof, for an enclosure. The sub-head, or rear disc thereof, can be releasably coupled to the open end 18 of the tube, such as by a pressure fit, press-fit, interference-fit, or the like. The sub-head 22 and tube or container 14 can form a seal, such as with the pressure fit, to resist premature release of scent. In addition, the sub-head 22 can have an enlarged front side 30 with a perimeter or flange that extends laterally or radially beyond the rear disc, and beyond the container or tube. The enlarged front side can abut to the open end of the container or tube when the rear disc is inserted therein. The enlarged front side can extend beyond or be disposed outside of the container or tube, and thus the enclosure. Thus, the sub-head or portion thereof, namely the front side, is disposed outside of the container or tube so that a supra-head, such as one of many different shapes and/sizes, can be affixed to the sub-head without removal from the container or tube, and without affecting a seal between the sub-head and the tube or container.

One or more vent rods 34, such as a pair of vent rods, extend from the back of the sub-head 22, and into the container or tube, or hollow thereof. The pair of vent rods can form a clip configured to be inserted through and engage an air vent when the tube is removed from the sub-head. The vent rods can have an opposite configuration with protrusions therebetween creating a narrower portion to resist inadvertent removal from the vent. In addition, the vent rods can have a cavity, indentation or elongated space formed between a distal protrusion on one end and the sub-head, or rear-disc thereof, on the opposite end. In one aspect, the sub-head 22 and the vent rods 34 can be integrally formed together at the same time as a monolithic body, such as by plastic in an injection molding process. In another aspect, the sub-head and the vent rods can be separately formed, and joined together, such as by adhesive, sonic welding, snap-fit, or the like.

One or more scented bodies 38, such as a pair of scented bodies, can be carried by and coupled to the vent rods 34. The scented bodies can be disposed in the cavity, indentation or elongated space of the vent rods. The scented bodies can have a scent material with a desired scent therein. For example, the scented bodies can be a material different from the vent rods, such as a gel, with a scented material, such as scented oil therein. The scented bodies can be sized and shaped similarly to the vent rods. The scented bodies extend into the container or tube with the vent rods, and are thus contained in the container or tube, or hollow thereof. The enclosure formed by the container or tube and the sub-head, or rear disc thereof, helps maintain the scent of the scented bodies and resist premature release of the scent. In addition, the scented bodies are insertable through the air vent with the vent rods, when the tube or container is removed from the sub-head. The scented bodies can be flush with or covered by the protrusions on the distal ends of the vent rods to resist interference upon insertion into the container or tube, or the air vent. The scent bodies can be coupled to the vent rods by a plurality of mating protrusions and indentations, with the protrusions formed on one of the pair of vent rods or the pair of scented bodies, and the indentations formed on the other of the pair of vent rods or the pair of scented bodies.

The container or tube 14, the sub-head 22, the vent rod(s) 34 and the scented body(ies) 38 can define an air freshener blank 42 (FIGS. 1*c*-6*b* and 8*a*-*c*) capable of receiving one of a plurality of different supra-heads 46 (FIGS. 1*a* and 1*b*, 7*a* and 7*b* and 15). The blank is defined without the supra-head or custom head; and is an operational, packaged, but unfinished air freshener. An air freshener 50 is defined by the sub-head 22, the supra-head 46, the vent rod(s) 34 and the scented body(ies) 38. The air freshener 50 can be removed from the container or tube 14, and the vent rod(s), with the scented body(ies), inserted through a vent of an air vent to provide a desired scent or neutralizing agent. Thus, the tube or container 14 can be removed from the sub-head 22, and thus the supra-head 46; and the vent rod(s) 34 and the scented body(ies) 38 can be inserted into an air vent, such as on a vehicle, so that the sub-head abuts the air vent and the supra-head is visible on the exterior of the air vent. As discussed below, the supra-head can carry indicia that is visible during use of the air vent. The air freshener blanks allow various different supra-heads to be selectively affixed to the blanks at the same or different times so that blanks can be produced and stored, while the supra-heads can be produced as needed, or can be changed.

The supra-head 46 has a back affixed to the front of the sub-head 22, and has a front with a face 54. Referring to FIGS. 7*a* and 7*b*, the face 54 can include a broad curvature across the head and face forming a dome 58. In one aspect, the dome 58 can be formed integrally with the supra-head. In another aspect, the dome 58 can be formed separately from the supra-head, and attached thereto such as by adhesive, sonic welding, snap-fit, press or interference fit, crimping, or the like. The dome and/or face can be transparent or translucent, while the supra-head can be opaque. The supra-head can include indicia 62, such as a logo, disposed between the supra-head and the dome, and visible therethrough. Alternatively, the indicia can be formed on the exposed face or surface of the dome.

The supra-head 46 can be sized larger than the sub-head 22, and can cover the sub-head 22 and the container or tube with respect to a view perpendicular to the face and collinear with a longitudinal axis of the container or tube. Thus, the supra-head can extend radially or laterally beyond the container or tube and the sub-head. The supra-head 46 is disposed outside of the container or tube. In addition, the supra-head can be a different size and/or shape than the sub-head. For example, while the sub-head can be circular, as show, the supra-head can be circular (46 in FIG. 1*a*), oval (46*b* in FIG. 7*a*), square (46*c* in FIG. 15*b*), rectangular, triangular, or any other shape (examples of which are shown in FIGS. 15*a*-d). The supra-head 46 can be affixed to the sub-head 22 using an adhesive, a snap-fit, a sonic weld, etc., while the sub-head is disposed in the opening of the tube or container, and without removing the air freshener from the tube or container. The front of the sub-head can include an indentation to receive a protrusion from the rear of the supra-head, and/or adhesive. The indentation can have a plurality of radial arms to maximize surface area to receive adhesive to secure the supra-head to the sub-head. The supra-head 46 can have a pair of flexible and resilient protrusions with enlarged and tapered ends that bend towards one another to press through an aperture in the sub-head, and then expand away from one another to retain the supra-head to the sub-head, defining a snap-fit. The snap-fit is one example of means for affixing the supra-head to the sub-head. Other means for affixing the supra-head to the sub-head can include adhesive, sonic welding, press or interference fit, crimping, or the like. As described above, the sub-head can be similarly affixed to the vent rod(s).

A method for providing custom air fresheners includes obtaining a plurality of air freshener blanks 42 as described above, and obtaining a plurality of custom supra-heads 46, also as described above. The plurality of custom supra-heads can include at least first and second pluralities of first and second custom supra-heads that are different from one another. The difference can include, size, shape, logo, color, and/or combinations thereof. The plurality of custom supra-heads can be affixed to the sub-heads of the plurality of blanks. The supra-heads can be affixed to the blanks while the sub-heads remain coupled to the containers. A larger supply of the plurality of blanks can be produced or fabricated than the supra-heads. In use, the tube or container 14 can be removed from the sub-head, and the vent rod(s) inserted through an air vent to the sub-head.

Referring to FIGS. 16*a*-18*c*, another air freshener device or air freshener blank 10*b* is shown that is similar in most respects to that described above, and which description is herein incorporated by reference. The air freshener further includes a bag 80 or sleeve disposed around and enclosing the vent rod(s) 38 and/or scented body(ies) 38, and between the vent rod(s) and/or scented body(ies) and the container or tube 14. The sleeve or bag 80 can have an bag opening 82 substantially concentric with the open end of the tube and/or the portion or rear disc of the sub-head. Thus, a perimeter of the bag opening can be disposed between a perimeter of the open end of the tube and the rear disc of the sub-head. A tab 84 is affixed to the bag and extends out of the container or tube through the open end between the portion of the sub-head releasably coupled across the open end of the container, or between the open end of the tube and the rear disc of the sub-head. The sleeve or bag can be formed of flexible plastic and can be at least translucent, such as a clear polymer. The bag can be placed on the vent rod, or the vent rod inserted into the bag, prior to insertion into the tube. The bag can seal around the scent material and/or scented bodies to help preserve the scent from escaping (along with the tube). In addition, the tab provides a pull tab extending out of the tube to use to remove the vent stick from the tube without pulling on the custom supra-head. The user can grab the tab with one hand and the tube with another hand, and pull to remove the vent stick from the tube packaging without having to pull on the custom supra-head.

Although the air freshener device has been shown and described as having a cylindrical container or tube with a circular opening closed by a circular disc of the sub-head, it will be appreciated that the container, opening and closure of the sub-head can have any shape, including for example, oval, square, rectangular, triangular, etc.

Although the air freshener device has been shown and described as having a desired scent or neutralizing agent, it will be appreciated that the scent material can include an agent to repel insects and/or animals, such as mosquitoes.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device, comprising:
   a) a container having an open end;
   b) a sub-head having a back with at least a portion of the sub-head releasably coupled across the open end of the container and closing the container, and having a front with an enlarged front side extending laterally beyond the container;
   c) a vent rod extending from the back of the sub-head and into the container, the vent rod being configured to be inserted through an air vent to the sub-head when the container is removed from the sub-head;
   d) a scent material having a desired scent carried by the vent rod and extending into the container with the vent rod and contained in the container by the sub-head, and being insertable through the air vent with the vent rod when the container is removed from the sub-head;
   e) the container, the vent rod and the scent material defining an air freshener blank capable of receiving one of a plurality of different supra-heads; and
   f) the one of a plurality of different supra-heads having a back affixed to the front of the sub-head and having a front with a face, the supra-head being sized larger than the sub-head and covering the sub-head, the supra-head being disposed outside of the container.

2. A device in accordance with claim 1, wherein the one of the a plurality of supra-heads is affixed to the sub-head after the vent rod is inserted into the container and after the sub-head is releasably coupled across the open end of the container.

3. A device in accordance with claim 1, wherein the container is substantially cylindrical.

4. A device in accordance with claim 1, wherein the container is at least translucent.

5. A device in accordance with claim 1, wherein the sub-head further comprises:
   a rear disc removably disposed in the open end of the container.

6. A device in accordance with claim 1, wherein the vent rod and the scent material further comprise:
   a pair of vent rods extending from the back of the sub-head and into the container, the pair of vent rods forming a clip configured to be inserted through and engage an air vent when the container is removed from the sub-head; and
   a pair of scented bodies having a scent material with a desired scent, each scented body sized similarly to a vent rod and each being carried by a different one of the pair of vent rods and extending into the container with the pair of vent rods and contained in the container, and being insertable through the air vent with the pair of vent rods when the container is removed from the sub-head.

7. A device in accordance with claim 6, wherein the pair of vent rods and the pair of scented bodies further comprise:
   a plurality of mating protrusions and indentations, with the protrusions formed on one of the pair of vent rods or the pair of scented bodies, and the indentations formed on the other of the pair of vent rods or the pair of scented bodies.

8. A device in accordance with claim 1, wherein the face of the supra-head includes a broad curvature across the head forming a dome.

9. A device in accordance with claim 1, wherein the supra-head includes indicia disposed between the supra-head and a dome disposed on the face, the dome being at least translucent.

10. A device in accordance with claim 1, further comprising means for affixing the supra-head to the sub-head.

11. A device in accordance with claim 1, further comprising:
   a bag disposed around the vent rod between the vent rod and the container; and
   a tab affixed to the bag and extending out of the container through the open end between the portion of the sub-head releasably coupled across the open end of the container.

12. An air freshener device, comprising:
   a) a tube having a substantially cylindrical wall with an open substantially circular end and a closed end, the cylindrical wall being at least translucent;
   b) a sub-head having a back with a substantially circular rear disc removably inserted into the open substantially circular end of the tube closing the tube, and having a front with an enlarged front side extending laterally beyond the rear disc;
   c) a pair of vent rods extending from the back of the sub-head and into the tube, the pair of vent rods forming a clip configured to be inserted through and engage an air vent when the tube is removed from the sub-head;
   d) a pair of scented bodies having a scent material with a desired scent, each scented body sized similarly to a vent rod and each being carried by a different one of the pair of vent rods and extending into the tube with the pair of vent rods and contained in the tube, and being insertable through the air vent with the pair of vent rods when the tube is removed from the sub-head;
   e) a bag extending around the pair of scented bodies and the pair of vent rods with a bag opening substantially concentric with the open end of the tube, and having a tab extending out of the container between the open end of the tube and the rear disc of the sub-head;

f) the tube, the sub-head, the pair of vent rods and the pair of scented bodies defining an air freshener blank capable of receiving one of a plurality of different supra-heads; and g) the one of a plurality of different supra-heads having a back affixed to the front of the sub-head and having a front with a face, the supra-head being sized larger than the sub-head and covering the sub-head, the supra-head being disposed outside of the tube.

13. A device in accordance with claim 12, wherein the pair of vent rods and the pair of scented bodies further comprise:
a plurality of mating protrusions and indentations, with the protrusions formed on one of the pair of vent rods or the pair of scented bodies, and the indentations formed on the other of the pair of vent rods or the pair of scented bodies.

14. A device in accordance with claim 12, wherein the face of the supra-head includes a broad curvature across the head forming a dome.

15. A device in accordance with claim 12, wherein the supra-head includes indicia disposed between the supra-head and a dome disposed on the face, the dome being at least translucent.

16. A device in accordance with claim 12, further comprising means for affixing the supra-head to the sub-head.

17. An air freshener device, comprising:
a) a tube having a substantially cylindrical wall with an open substantially circular end and a closed end, the cylindrical wall being at least translucent;
b) a sub-head having a back with a substantially circular rear disc removably inserted into the open substantially circular end of the tube closing the tube, and having a front with an enlarged front side extending laterally beyond the rear disc;
c) a pair of vent rods extending from the back of the sub-head and into the tube, the pair of vent rods forming a clip configured to be inserted through and engage an air vent when the tube is removed from the sub-head;
d) a pair of scented bodies having a scent material with a desired scent, each scented body sized similarly to a vent rod and each being carried by a different one of the pair of vent rods and extending into the tube with the pair of vent rods and contained in the tube, and being insertable through the air vent with the pair of vent rods when the tube is removed from the sub-head;
e) the tube, the sub-head, the pair of vent rods and the pair of scented bodies defining an air freshener blank capable of receiving one of a plurality of different supra-heads; and
f) the one of a plurality of different supra-heads having a back affixed to the front of the sub-head and having a front with a face, the supra-head being sized larger than the sub-head and covering the sub-head, the supra-head being disposed outside of the tube.

18. A device in accordance with claim 17, further comprising:
a bag extending around the pair of scented bodies and the pair of vent rods with a bag opening substantially concentric with the open end of the tube, and having a tab extending out of the container between the open end of the tube and the rear disc of the sub-head.

19. A device in accordance with claim 17, wherein the pair of vent rods and the pair of scented bodies further comprise:
a plurality of mating protrusions and indentations, with the protrusions formed on one of the pair of vent rods or the pair of scented bodies, and the indentations formed on the other of the pair of vent rods or the pair of scented bodies.

20. A device in accordance with claim 17, wherein the face of the supra-head includes a broad curvature across the head forming a dome.

21. A device in accordance with claim 17, wherein the supra-head includes indicia disposed between the supra-head and a dome disposed on the face, the dome being at least translucent.

* * * * *